United States Patent
Bartels et al.

(10) Patent No.: US 6,854,140 B2
(45) Date of Patent: Feb. 15, 2005

(54) MEDICAL EXAMINATION/TREATMENT SYSTEM WITH MULTIPLE PATIENT BEDS, AND TRANSPORT CARRIAGE THEREFOR

(75) Inventors: Frank Bartels, Seybothenreuth (DE); Michael Heinold, Speichersdorf (DE); Rolf Reimann, Forchheim (DE)

(73) Assignee: Siemens Aktiengesellschaft, Münich (DE)

( * ) Notice: Subject to any disclaimer, the term of this patent is extended or adjusted under 35 U.S.C. 154(b) by 0 days.

(21) Appl. No.: 10/472,121

(22) PCT Filed: Mar. 7, 2002

(86) PCT No.: PCT/DE02/00824

§ 371 (c)(1),
(2), (4) Date: Sep. 16, 2003

(87) PCT Pub. No.: WO02/076298

PCT Pub. Date: Oct. 3, 2002

(65) Prior Publication Data

US 2004/0102690 A1 May 27, 2004

(30) Foreign Application Priority Data

Mar. 21, 2001 (DE) .......................................... 101 13 855

(51) Int. Cl.[7] ............................................... A61B 6/04
(52) U.S. Cl. .............................. 5/601; 5/600; 5/81.1 R; 5/86.1; 378/209
(58) Field of Search ........................... 5/600, 601, 86.1, 5/81.1 R; 378/209

(56) References Cited

U.S. PATENT DOCUMENTS

| 3,917,076 | A |   | 11/1975 | Campbell |       |
|-----------|---|---|---------|----------|-------|
| 5,014,968 | A | * | 5/1991  | Lammers et al. | 5/611 |
| 5,475,884 | A |   | 12/1995 | Kirmse et al. |     |
| 5,842,987 | A |   | 12/1998 | Sahadevan |        |
| 6,101,644 | A |   | 8/2000  | Gagneur et al. |    |
| 6,205,347 | B1|   | 3/2001  | Morgan et al. |     |
| 6,640,364 | B1| * | 11/2003 | Josephson et al. | 5/601 |
| 2002/0174485 | A1 | * | 11/2002 | Bartels | 5/601 |
| 2004/0143905 | A1 | * | 7/2004 | Pastyr et al. | 5/601 |

FOREIGN PATENT DOCUMENTS

DE 3123926 A1 * 1/1983 ............ A61B/6/04

* cited by examiner

Primary Examiner—Teri Pham Luu
(74) Attorney, Agent, or Firm—Schiff Hardin LLP

(57) ABSTRACT

A transport carriage for a patient bed has a first arm for placement of the patient bed thereon and a second arm for coupling the patient bed thereto. A medical treatment of examination system employing such a transport carriage has a number of medical devices for treatment of examination of a subject, each of these medical devices having a patient support mechanism associated therewith, with a differently configured patient bed. The patient beds are removable from the respective support mechanisms, and the transport carriage is configured to receive and transport any of these differently configured patient beds.

14 Claims, 4 Drawing Sheets

MEDICAL EXAMINATION/TREATMENT SYSTEM WITH MULTIPLE PATIENT BEDS, AND TRANSPORT CARRIAGE THEREFOR

BACKGROUND OF THE INVENTION

1. Field of the Invention

The present invention is directed to a system for the medical examination and/or treatment of a patient, having a number of examination and/or treatment devices of different types, particularly having a magnetic resonance tomography device and/or a computed tomography device and/or an angiography device and/or a nuclear therapy device, wherein each of the examination and/or treatment devices has a patient support mechanism with a patient bed, wherein the respective patient bed can be introduced into an examination and/or treatment area of the respective examination and/or treatment device, and having at least one transport gurney.

The invention is also directed to a transport carriage for a patient bed, particularly for a system for medical examination and/or treatment of a patient of the above type, an undercarriage and comprising extension arms for the acceptance of the patient bed.

2. Description of the Prior Art

Transport carriages that enable the transfer of a patient to a table stand of an examination device are disclosed, for example, in German OS 30 34 932 and German PS 42 24 036.

A number of different medical examination devices and/or a number of different treatment devices are usually present in a large hospital. Each examination and/or treatment device has a specific patient support mechanism with a patient bed that is attached to a pedestal either rigid in position or movable. The patient lies on the patient bed during the examination or treatment. In order to introduce the patient into the examination or treatment region of the particular examination and/or treatment device, for example into the bore of a magnetic resonance tomography device, the patient bed is, in particular, movably seated or guided on the pedestal.

A transport carriage that is also referred to as gurney is used for the transport to or from an examination and/or treatment device. The patient is placed or bedded on the gurney for this purpose. A re-bedding or repositioning procedure is thereby necessary, this being time-consuming and physically strenuous for the medical personnel. Moreover, highly impaired patients, for example trauma patients, can suffer further impairment during a re-bedding procedure. Valuable time is also lost during the re-bedding.

SUMMARY OF THE INVENTION

An object of the invention is to provide an examination and/or treatment device wherein these disadvantages are avoided or at least alleviated. It is also an object to provide a gurney for the same purpose.

The first object is inventively achieved in a system of the type initially described wherein the respective patient beds are removable from the respective patient, and wherein each patient bed and the transport carriage are fashioned such that each of the patient beds can be coupled to the transport carriage.

The inventive system has the advantage that the patient can already be borne on the patient bed needed for the respective examination and/or treatment device and the patient support mechanism thereof when traveling to or from an examination and/or treatment device. The number of necessary re-bedding or repositioning events is thus advantageously reduced for the hospital personnel. The hospital personnel can work more efficiently and less strenuously in ergonomic terms. Because each of the patient beds can be coupled to the transport carriage, this advantage can be achieved without requiring an especially large number of different transport gurneys. This means that the probability that the hospital personal will find a suitable transport carriage at a specific location of examination or treatment room in the hospital is high, even given only a small number of available gurneys.

The patient beds, in particular, can be firmly coupled to the transport carriages, i.e. lifting and shifting of the patient bed on the transport carriage is suppressed in the coupled condition. Motion in all six spatial directions is suppressed in the coupled condition. The coupling can occur with a frictional connection and/or interlocking.

The patient beds can also be coupled at least to the patient support mechanism of their respective examination and/or treatment device.

In a preferred embodiment, the patient beds and the gurney are fashioned such that the patient beds can be placed on the transport carriage at one end thereof and can be coupled thereto at the opposite end. In this embodiment, thus, a firm (positive) connection between the patient beds and the gurney is produced at only one end of the transport carriage. A number of advantages gurney therefrom. First, the patient beds need not be provided with a coupling mechanism (which would possibly have to be fabricated of metal) at the end at which they can be placed onto the transport carriage. This assures that this end of the patient beds can be introduced, for example, into the opening of a magnetic resonance tomography device or of a computed tomography device without disrupting its operation (magnetic field or X-ray absorption or the like). Another advantage is that—proceeding from a known examination and/or treatment device with a permanently allocated patient bed—the patient bed need not be modified at the one side, at least not significantly. This is of significance for a retrofitting existing medical examination and/or treatment devices. There is also the advantage given a placement of the patient bed at the one end of the gurney that the gurney can be designed such that an impediment for the hospital personnel is avoided, i.e. the patient is optimally accessible.

The patient beds and the transport carriage preferably are coupled at the foot end of the patient. It is likewise preferred that the patient beds be placed onto the transport carriage at the head end of the patient.

According to a preferred embodiment, the patient beds have identical coupling devices for releasable fastening to the gurney. These coupling devices can also be fashioned for the coupling to the patient support mechanisms of the examination and/or treatment devices.

To this end, the gurney preferably has a coupling for the acceptance of the coupling device of the patient beds, so each patient bed is releasable from the transport carriage by actuating the coupling. An advantage of this version is that the majority part of the coupling mechanism can be attached to the gurney and that the patient beds—which likewise already exist—need be only slightly modified.

The second object directed to a gurney is inventively achieved in a gurney of the type initially described wherein a first of the extension arms is fashioned for the non-coupling placement of the patient bed, and a second of the extension arms is fashioned for coupling the patient bed.

Such a gurney can be fashioned especially easily for universal employment for a number of medical examination and/or treatment devices. The underside of that side of the patient bed coming to lie on the first extension arm need not be modified at all or only slightly. A coupling mechanism that could disrupt the imaging in an X-ray device, computed tomography device or nuclear magnetic resonance device because it is fabricated of metal is not needed.

The access to the patient at this side of the patient bed also remains unrestricted. For this reason as well, the first extension arm preferably is attached at the head end of the patient, i.e. the part of the patient bed at which the head of the patient is intended to be located.

The second extension arm preferably is fashioned such that the patient bed comes to lie under the second extension arm in the coupled condition. In this way, it becomes advantageously possible to retrofit an existing patient bed in a simple way without having to intervene at its underside, which is usually specifically adapted to the respective patient support mechanism.

In particular, the second extension arm is fashioned for accepting the patient bed in suspended fashion. However, versions are also possible wherein the second extension arm holds the patient bed engaging under or grasping its upper side.

Particularly given the suspended acceptance of the patient bed, it is expedient for the second extension arm to have a coupling for producing a rigid, releasable connection to the patient bed. Such a coupling can be realized in a simple way, for example by a catch or snap-in mechanism.

The engagement of the second extension arm to the patient bed, particularly to the coupling, can occur with a frictional connection and/or interlock, particularly such that the patient bed cannot be moved either to the side or up or down in the coupled condition.

In the gurney of the invention, in contrast, such a rigid connection to the patient bed can be omitted at the first extension arm. The first extension arm preferably is fashioned such that the patient bed lying thereon is secured against lateral dislocation, preferably such that the patient bed remains movable in the upward direction. This has the advantage that attaching the patient bed on the transport carriage is simplified for the hospital personnel. It also is an advantage that a coupling device that could disrupt the imaging in an examination device—particularly when fabricated of metal—is not compulsory at the head end of the patient bed, i.e. at the side of the first extension arm.

The first extension arm preferably has a recess for the patient bed the underside of which, in particular, is equipped with an appliance that fits into the recess with a form fit and may latch thereto.

In a preferred embodiment the two extension arms have their respective ends secured to a telescoping column. As a result, it is advantageously possible to adapt the gurney to the respective support height of the appertaining examination and/or treatment device in the transfer to or from one of the examination and/or treatment devices. Different device heights must be expected in the utilization of the inventive gurney with a number of examination and/or treatment devices that differ in type.

It is advantageous for the telescoping columns to be eccentrically attached on the undercarriage, particularly to the edge side of the undercarriage. The load-bearing structure of such a gurney composed, among other things, of the undercarriage, the telescoping columns and the support arms has, in particular, the shape of a rectangle open at one side or of a "C" as viewed in cross-section. It is especially advantageously possible with such a gurney to a transfer the patient bed to an examination and/or treatment device or fetch it therefrom without needing a critical lateral displacement of the patient bed. With such a gurney, on the contrary, it is especially advantageously possible given a transfer of the patient bed from the gurney to an examination and/or treatment device to position the patient bed exactly at that location over a pedestal of the patient support mechanism at which the patient bed can be coupled to the sub-structure or pedestal of the patient support mechanism. The load-bearing structure of the gurney can thereby embrace stationary parts of the respective patient bearing mechanism. These parts are then positioned in the inside of the open rectangle "C".

In another preferred embodiment, the telescoping columns are height-adjustable in tandem as well as independently of one another. A gurney designed in this way has the specific advantage that it can accept patient beds of different thickness or height. This is especially significant when, in the coupled condition of the patient bed, the first extension arm is arranged under the patient bed and the second extension arm is arranged above the patient bed.

The extension arms preferably can be removed from the undercarriage and be interchanged with one another. Since, for example, the back extension arm is attachable to the front position and the front extension arm is attachable to the back position, the advantage is achieved that the gurney can optionally approach a patient support mechanism from the left or from the right, and it is always assured that the first extension arm can be placed facing the examination area of an examination device, for example the opening of a magnetic resonance tomography device.

DESCRIPTION OF THE PREFERRED EMBODIMENTS

Figure 1:
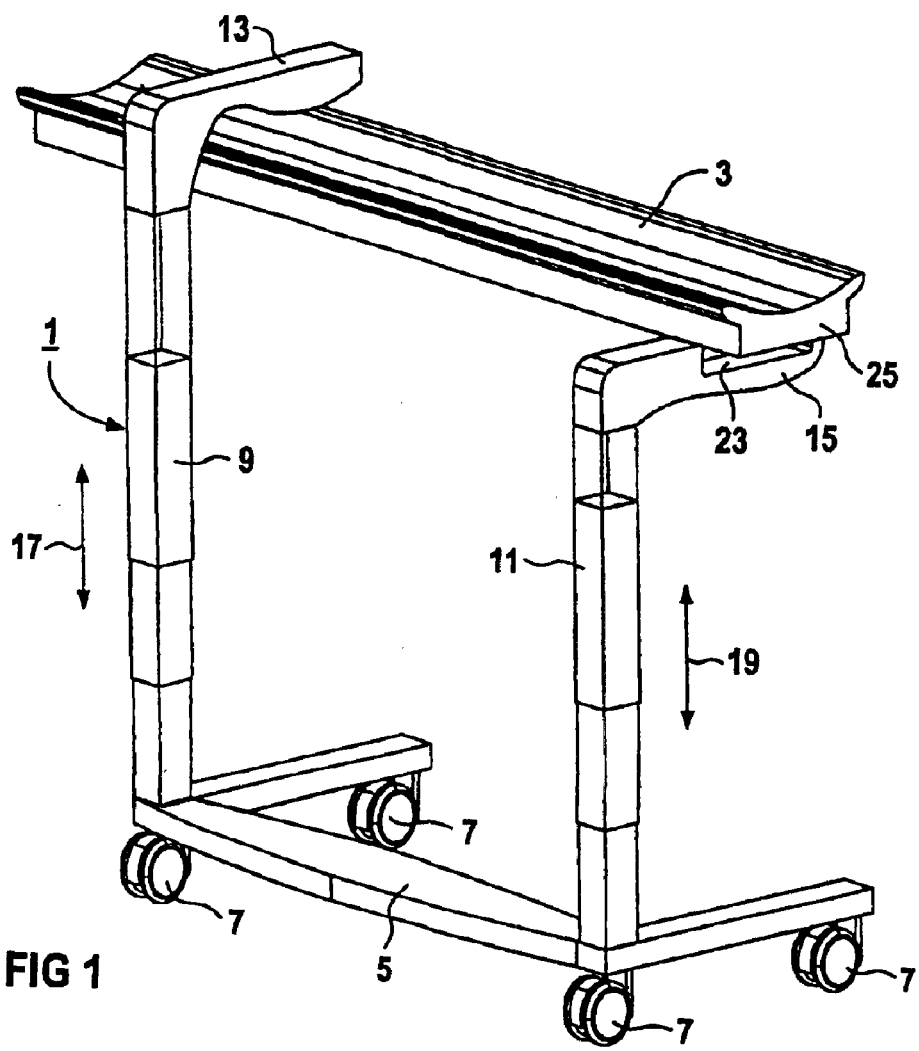
FIG. 1 is a perspective illustration of a transport carriage in accordance with the present invention.

FIG. 1 shows a gurney or a transport carriage 1 for the acceptance of a couchette board, a trauma plate, a patient support plate or a patient bed 3. At the bottom, the transport carriage 1 has a U-shaped or C-shaped undercarriage 5 to which four double rollers 7 are attached. Two of the double rollers 7 can be locked by actuating a foot switch (not shown).

Telescoping columns 9, 11 are attached to the edge at the closed side of the undercarriage 5, the telescoping columns 9, 11 being adjustable in height both in tandem as well as independently of one another either manually or by means of a drive motor (not shown). The telescoping columns 9, 11 respectively carry horizontally proceeding extension arm 13 and 15. The extension arms serve for the acceptance of the patient bed 3, whereby the first extension arm 15 supports the patient bed 3 and the second extension arm 13 engages the bed 3 from above. Patient beds 3 of different thickness can be transported with the transport carriage 1 in that the telescoping columns 9, 11 are extensible independently of one another along the vertical directions 17 and 19, even though the second extension arm engages at the patient bed 3 from above and the first extension arm 15 engages from below.

The first extension arm 15 is fashioned for placement of the patient bed 3 thereon and has a depression or a broad recess 23 at its upper side for this purpose, the depression or broad recess 23 accepting a corresponding appliance 25 at the underside of the patient bed 3 such that the patient bed 3 is secured against lateral dislocation at the location of the first extension arm 15. The transport carriage 1 and the patient bed 3 are fashioned such that the head of a patient comes to lie at the first extension arm 15 and the patient's feet come to lie at the second extension arm 13.

The first extension arm 15 and the second extension 13 are secured to the undercarriage 5 by means of identical plug-type connectors (not shown), so that they can be interchanged with one another. Locking pins, for example, are present for the detent.

Figure 2:
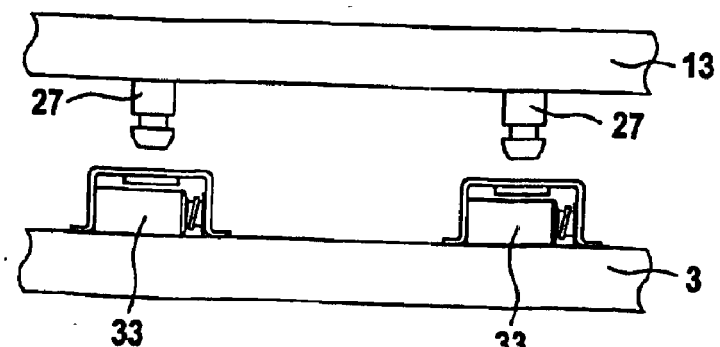
FIG. 2 show a detail of the transport carriage of FIG. 1.

The second extension arm 13 is fashioned for rigid coupling of the patient bed 3. A possible coupling mechanism is shown in greater detail in FIG. 2. The second extension arm 13 has a coupling 27 that can be coupled to corresponding coupling devices 33 at the upper side of the patient bed 3 rigid in position and releasable. In the illustrated example, the coupling 27 is formed as pegs fashioned conically at their tip with an annular channel arranged therebehind. As cooperating members, these pegs can be engaged into the respective coupling device 33 wherein a spring-loaded pin engages into the annular channel.

Figure 3:
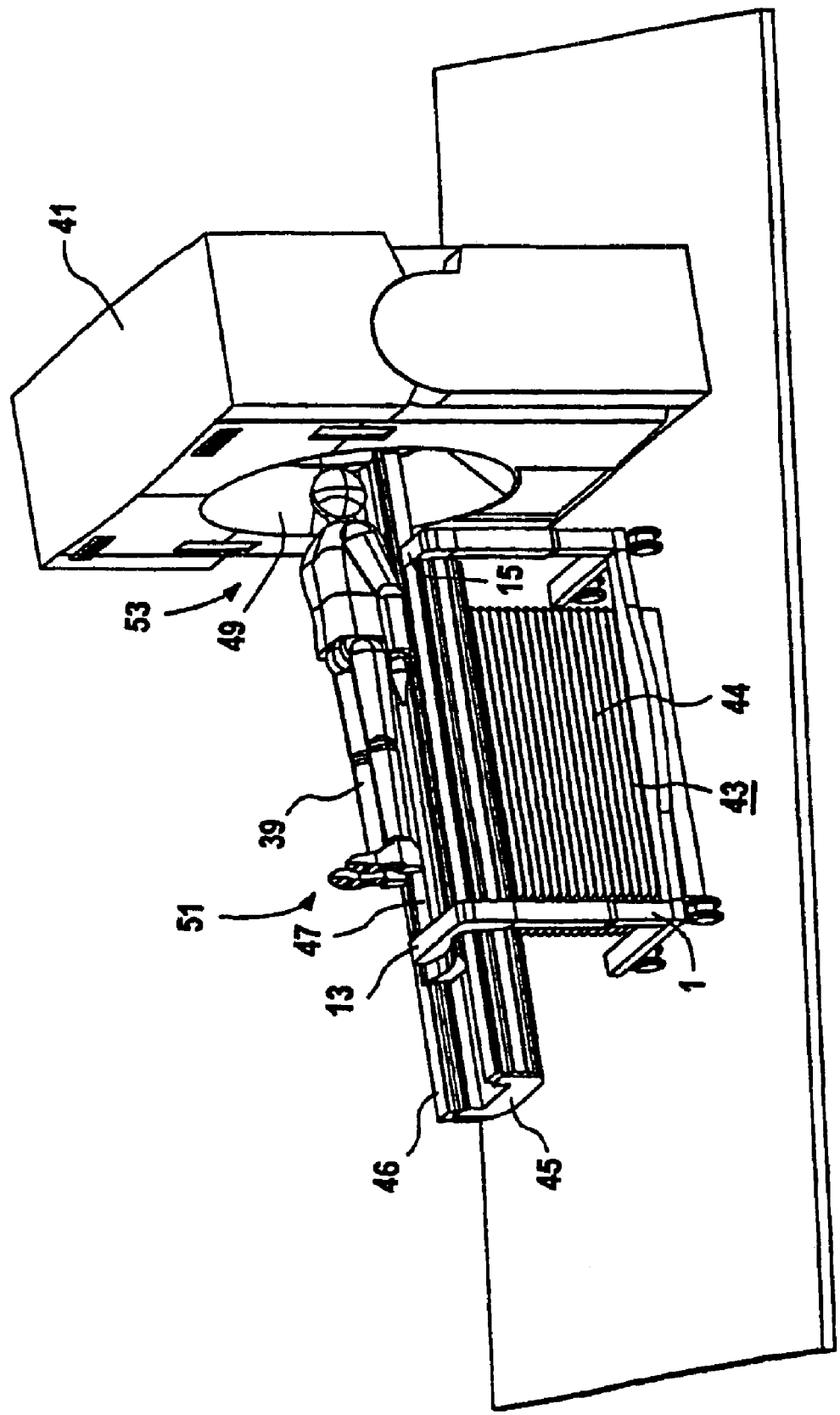
FIG. 3 shows the transport carriage of FIG. 1 employed at a computed tomography device.
Figure 4:
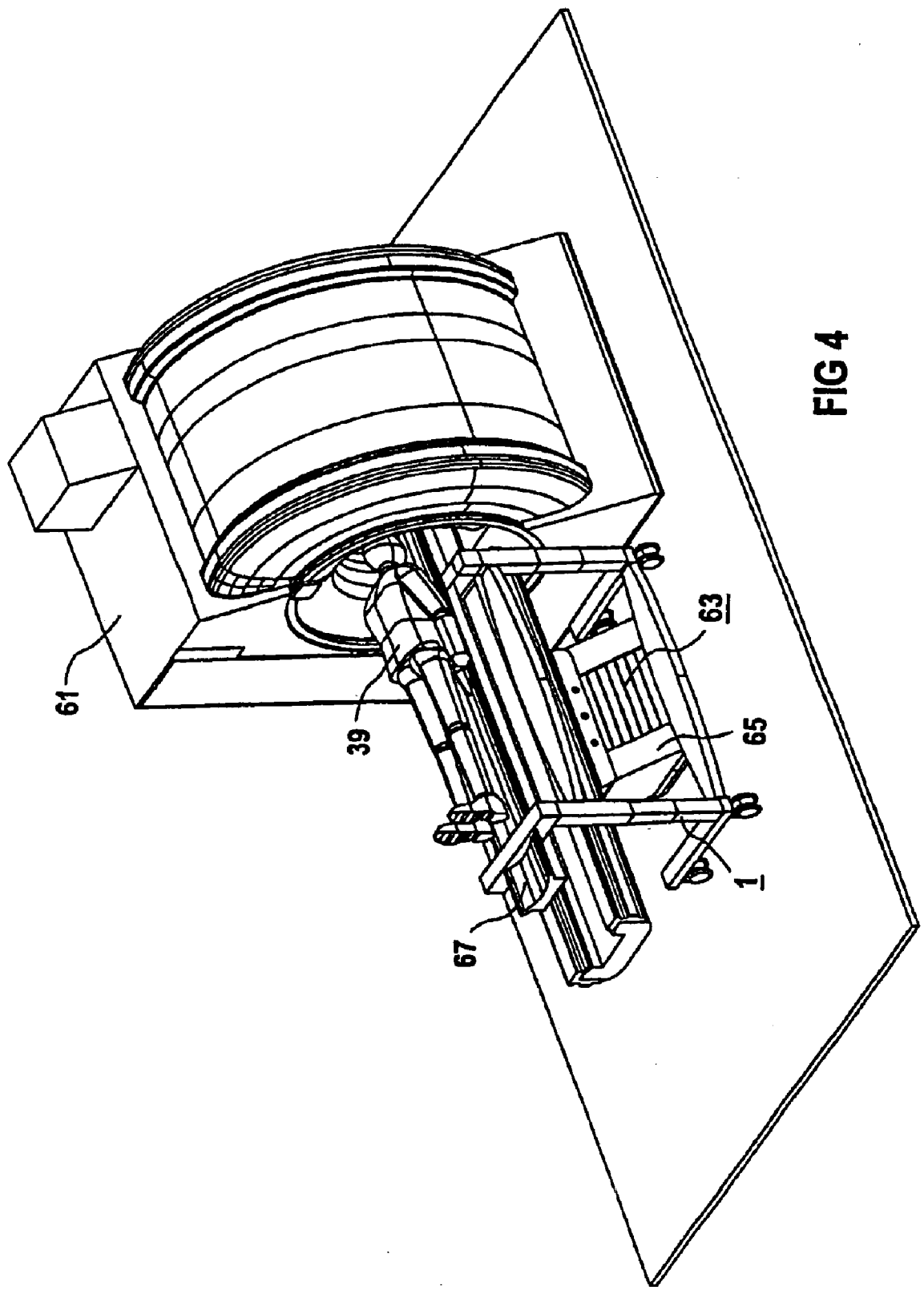
FIG. 4 shows the transport carriage of FIG. 1 employed at a magnetic resonance tomography device.
Figure 5:
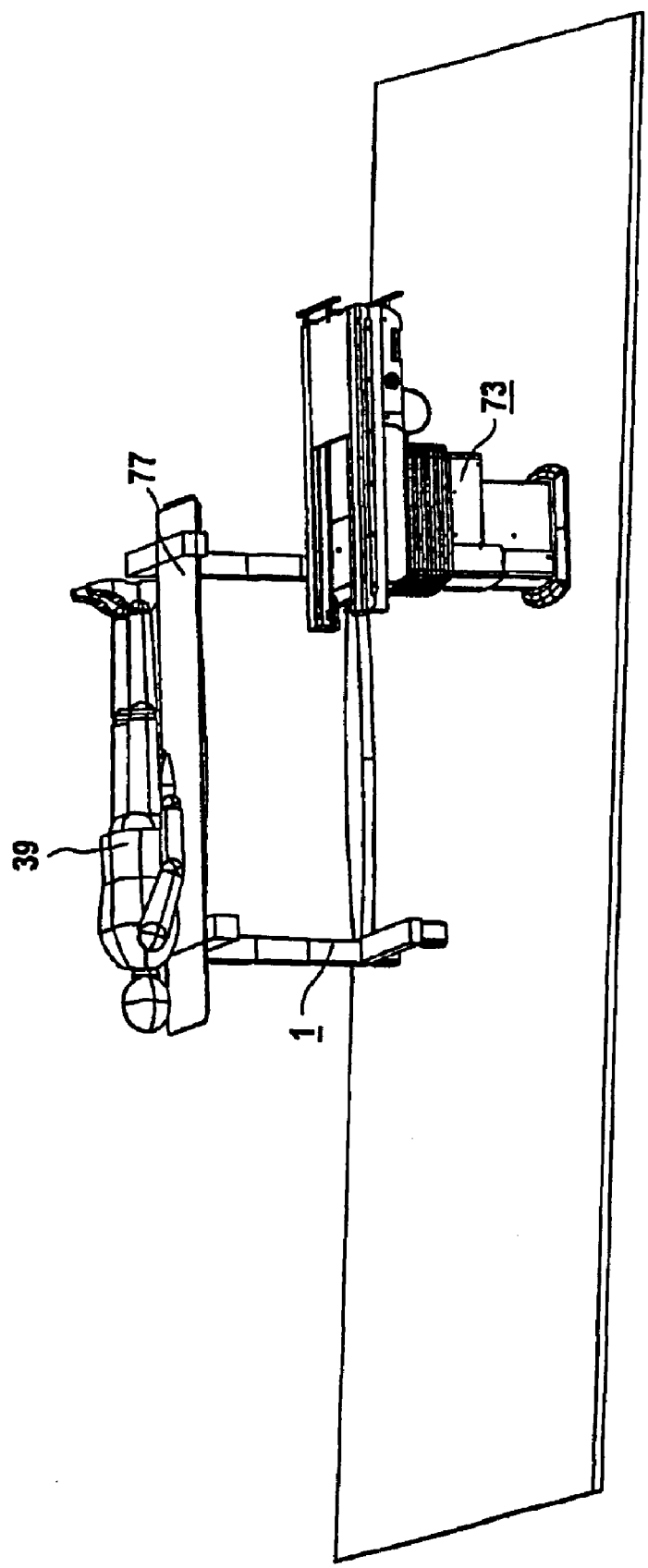
FIG. 5 shows the transport carriage of FIG. 1 in another employment thereof.

FIGS. 3, 4 and 5 schematically show the employment of the transport carriage 1 of the invention at different medical examination devices.

FIG. 3 shows a patient 39 before examination in a computed tomography device 41. The computed tomography device 41 includes a patient support mechanism 43 that has a pedestal 44 with an oblong, projecting upper part 45 arranged thereon. A carriage 46 is movable in longitudinal direction in the upper part 45. The carriage 46 is fashioned for the acceptance of a patient bed 47, so that the patient bed 47 with a patient 39 lying thereon is introducible into an opening 49 in the housing of the computed tomography device 41. A scan over a number of tomograms occurs by moving the patient 39 through the opening 49. The patient bed can be removed in a simple way by the medical personnel, preferably by being lifted slightly up.

The carriage itself can also be fashioned as support plate or bed.

FIG. 3 shows the transport carriage 1 with the patient bed 47 immediately before or after a transfer from or to the patient support mechanism 43. In order to arrive in this position, the patient 49 was previously moved into the examination room with the computed tomography device 41 by means of the transport carriage 1. The transport carriage 1 was then positioned at the patient support mechanism 43 under the upper part 45 and embracing the pedestal 44. The first extension arm 15 was thereby positioned at the head end of the patient support mechanism 43, so that the patient 39 can be introduced head first into the opening 49. The first extension arm 15 is thereby arranged between the end of the patient bearing mechanism 43 at the housing side and the housing of the computed tomography device 41 and supports the patient bed 47. At this point in time, the patient bed 47 is still attached to the second extension arm 13 at the foot end 51. At this point in time, the two telescoping columns 9, 11 can be extended to different distances in height if the thickness of the patient bed 47 (=distance between upper edge and bottom edge) requires this.

For transferring the patient bed 47 to the patient support mechanism 43, the telescoping columns 9, 11 are then simultaneously retracted until the patient bed 47 comes to lie on the carriage 46 and can be coupled thereto as warranted.

After the transfer of the patient bed 47 to the patient support mechanism 43, the telescoping column 9 of the second extension arm 43 is moved upward and the telescoping column 11 of the first extension arm 15 is moved downward, so that the transport carriage 1 can be moved away from the patient support mechanism 43. As an alternative, the upper edge of the patient support mechanism 43 is moved downward.

FIG. 4 shows the patient 39 before an examination in a magnetic resonance tomography device 61 having a patient support mechanism 63 that has a patient bed 67. As is the case for all patient beds of the inventive system, the patient bed 67 can be removed by the personnel.

Using the patient support mechanism 63, the patient 39 lying on the patient bed 67 is introduced into an opening 69 of a magnet of the magnetic resonance tomography device 61, the opening having an examination region, so that a 3D image can be acquired therein. The patient support mechanism 63 of the illustrated magnetic resonance tomography device 61 has a pedestal 65 that is spaced approximately 30 cm from the housing of the magnetic resonance tomography device 61. As a cantilevered region of the patient bed 67, the distance is of particular advantage because the transfer of the bed 67 is simplified.

FIG. 5 shows a further application of the transport carriage 1 for a differently configured patient support mechanism 73 having an allocated, removable patient bed 77.

At the foot end, the patient beds 47, 67, 77 allocated to the respective patient support mechanisms 43, 63, 73 of FIGS. 3 through 5 are respectively provided with a coupling device that is accessible from above and the same compared to the second extension arm 13, so that the interface between the patient beds 47, 67, 77 and the transport carriage 1 is the same for each. The transport carriage 1 can thus be universally employed. In other words, all patient beds 47, 67, 77 of the combination of different examination devices can be coupled to the at least one transport carriage 1.

The system formed by a combination of the computed tomography device 41, the magnetic resonance tomography device 61 and a further X-ray device (angiography device) that is not shown (FIG. 5) and also including the transport carriage 1 represents a system according to the invention for the medical examination of a patient. Only a small number of transport carriages 1 are required within this system and there is a high probability that are transport carriage will always be available since these are universally employable.

It is of particular advantage within the system for each of the patient beds 47, 67, 77 to be fashioned such that it can be coupled to each of the patient support mechanisms 43, 63, 73, i.e. the coupling mechanism of each patient bed 47, 67, 77 to the sub-structure is identical. The number of required re-bedding or repositioning events for the patient 39, who must undergo a plurality of examinations at various examination devices 41, 61 ("modalities"), is minimized given this configuration.

A special advantage of the transport carriage 1 of the invention is the possibility of designing all known patient beds with only slight modifications for the trolley mode without having to intervene in the basic design or the basic structure of the respective patient bed or the respective patient bearing mechanism. The specific way of attaching the patient bed on the transport carriage 1 assures a maximum accessibility to the patient for the hospital personnel and for mobile fluoroscopy devices that may be potentially present. The transport carriage 1 also allows a retention of the modality-specific shape of known patient beds at the head end without having to fear limitations of the modality-specific image quality.

Either additionally or instead, for example, a nuclear therapy device or a lithotripsy device can be present as examination and/or treatment device.

Although modifications and changes may be suggested by those skilled in the art, it is the invention of the inventors to embody within the patent warranted heron all changes and modifications as reasonably and properly come within the scope of their contribution to the art.

What is claimed is:

1. A medical examination/treatment system comprising:
   a plurality of medical devices selected from the group consisting of examination devices and treatment devices, each of said medical devices having a region adapted to interact with a patient and a patient support mechanism, each patient support mechanism having a patient bed removably engageable therewith adapted to receive a patient thereon with the head of the patient disposed at a first end of the patient bed and the feet of the patient disposed at a second, opposite end of the patient bed, each support mechanism being operable to move the patient support bed into and out of said region of the associated medical device, and each of said patient beds for the respective support mechanisms associated with the respective medical devices being differently configured; and
   a transport carriage movable independently of each of said medical devices for transporting the respective patient beds to and from the respective medical devices, said transport carriage being configured to receive each of said differently configured patient beds, with the first end of each patient bed being disposed in non-coupling fashion with a first end of said transport carriage and the second end of each of said patient beds being coupled to said transport carriage at a second opposite end of said transport carriage.

2. A system as claimed in claim 1 wherein each of said differently configured patient beds has a coupling device for releasably fastening the respective patient bed to the second end of the transport carriage, with the respective coupling devices of the differently configured patient beds being identical.

3. A system as claimed in claim 2 said transport carriage comprises a coupling arrangement at said second end configured to accept said identical coupling devices of the differently configured patient beds, allowing a patient bed on said transport carriage to be released from coupling with said transport carriage by actuating said coupling arrangement.

4. A transport carriage for use with a plurality of differently configured patient beds, comprising:
   an undercarriage;
   first and second extension arms adapted to receive a patient bed; and
   a first of said extension arms receiving said patient bed thereon in non-coupling fashion, and a second of said extension arms being configured to couple a patient bed thereto, with the patient bed received beneath said second extension arm.

5. A transport carriage as claimed in claim 4 wherein said second of said extension arms receives the patient bed in suspended fashion.

6. A transport carriage as claimed in claim 4 wherein said second extension arm comprises a coupling arrangement adapted to interact with the patient bed to produce a rigid, releasable connection to the patient bed.

7. A transport carriage as claimed in claim 4 wherein said first of said extension arms is configured to secure a patient bed disposed thereon against lateral dislocation.

8. A transport carriage as claimed in claim 7 wherein said first of said extension arms is configured to prevent said lateral dislocation while allowing the patient bed to be moved upwardly relative to said first of said extension arms.

9. A transport carriage as claimed in claim 7 wherein said first of said extension arms comprises a recess for preventing said lateral dislocation.

10. A transport carriage as claimed in claim 4 further comprising a first telescoping column to which said first of said extension arms is attached, and a second telescoping column to which said second of said extension arms is attached.

11. A transport carriage as claimed in claim 10 wherein said telescoping columns are eccentrically attached to said undercarriage.

12. A transport carriage as claimed in claim 11 wherein said telescoping columns are attached at an edge side of said undercarriage.

13. A transport carriage as claimed in claim 10 wherein said first and second telescoping columns are adjustable in height independently of each other as well as in tandem.

14. A transport carriage as claimed in claim 4 wherein said first of said extension arms and said second of said extension arms are removably and interchangeably attached to said undercarriage.

* * * * *